(12) United States Patent
Jonckers et al.

(10) Patent No.: US 8,318,779 B2
(45) Date of Patent: Nov. 27, 2012

(54) LYSINE RELATED DERIVATIVES AS HIV ASPARTYL PROTEASE INHIBITORS

(75) Inventors: Tim Hugo Maria Jonckers, Edegem (BE); Inge Dierynck, Berchem (BE); Stefaan Julien Last, Lint (BE); Herman De Kock, Arendonk (BE)

(73) Assignee: Janssen R&D Ireland, Little Island (IE)

( * ) Notice: Subject to any disclaimer, the term of this patent is extended or adjusted under 35 U.S.C. 154(b) by 268 days.

(21) Appl. No.: 12/300,211

(22) PCT Filed: May 30, 2007

(86) PCT No.: PCT/EP2007/055230
§ 371 (c)(1),
(2), (4) Date: Nov. 10, 2008

(87) PCT Pub. No.: WO2007/138069
PCT Pub. Date: Dec. 6, 2007

(65) Prior Publication Data
US 2009/0118339 A1    May 7, 2009

(30) Foreign Application Priority Data
May 30, 2006  (EP) .................................. 06114672

(51) Int. Cl.
*A61K 31/44*  (2006.01)
*A61K 31/165*  (2006.01)
*C07C 237/14*  (2006.01)
*A61P 31/14*  (2006.01)
*C07D 211/72*  (2006.01)

(52) U.S. Cl. ......... 514/345; 514/619; 546/337; 564/164

(58) Field of Classification Search ................ None
See application file for complete search history.

(56) References Cited

U.S. PATENT DOCUMENTS
2006/0025592 A1    2/2006    Stranix et al.

FOREIGN PATENT DOCUMENTS
WO          02/064551 A1    8/2002

OTHER PUBLICATIONS

Stranix et al.2, caplus an 2003:810108.*
Chou, T.C., et al., "Quantitative Analysis of Dose-Effect Relationships: The Combined Effects of Multiple Drugs or Enzyme Inhibitors", Advanced Enzyme Regulations, (1984), vol. 22, pp. 27-55.
Hertogs, K., et al., "A Rapid Method for Simultaneous Detection of Phenotypic Resistance to Inhibitors of Protease and Reverse Transcriptase in Recombinant Human Immunodeficiency Virus Type 1 Isolates From Patients Treated With Antiretroviral Drugs", Antimicrobial Agents and Chemotherapy, (1998), vol. 42, No. 2, pp. 269-276.
Stranix, B.R., et al., "Lysine Sulfonamides As Novel HIV-Protease Inhibitors: Nε-Acyl Aromatic α-Amino Acids", Bioorganic & Medicinal Chemistry Letters, (2006), vol. 16, No. 13, pp. 3459-3462.
International Search report for Application No. PCT/EP2007/055230 mailed Aug. 16, 2007.

* cited by examiner

Primary Examiner — Sun Jae Loewe

(57) ABSTRACT

The present invention concerns lysine related derivatives, their use as protease inhibitors, in particular as HIV aspartyl protease inhibitors, processes for their preparation as well as pharmaceutical compositions and diagnostic kits comprising them. The present invention also concerns combinations of the present lysine related derivatives with another anti retroviral agent. It further relates to their use in assays as reference compounds or as reagents.

21 Claims, No Drawings

LYSINE RELATED DERIVATIVES AS HIV ASPARTYL PROTEASE INHIBITORS

CROSS REFERENCE TO RELATED APPLICATIONS

This application is the national stage of PCT Application No. PCT/EP2007/055230, filed May 30, 2007, which claims priority from European Patent Application No. 06114672.6, filed May 30, 2006, the entire disclosures of which are hereby incorporated in their entirely.

The present invention relates to lysine related derivatives, their use as protease inhibitors, in particular as HIV aspartyl protease inhibitors, processes for their preparation as well as pharmaceutical compositions and diagnostic kits comprising them. The present invention also concerns combinations of the present lysine related derivatives with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by aspartic protease. For instance the HIV viral gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), fusion inhibitors such as T-20 or other protease inhibitors. Despite the fact that these antiretrovirals are very useful, they have a common limitation, namely, the targeted enzymes in HIV are able to mutate in such a way that the known drugs become less effective, or even ineffective against these mutant HIV viruses. Or, in other words HIV creates an ever-increasing resistance against the available drugs.

Resistance of retroviruses, and in particular HIV, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV, but also on the increasingly more common resistant HIV.

Known antiretrovirals, often administered in a combination therapy regimen, will eventually cause resistance as stated above. This often may force the physician to boost the plasma levels of the active drugs in order for said antiretrovirals to regain effectivity against the mutated HIV. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favourable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Hitherto several protease inhibitors are on the market or are being developed like, for instance, amprenavir (APV), saquinavir (SQV), indinavir (IDV), ritonavir (RTV), nelfinavir (NFV), lopinavir (LPV) and darunavir (TMC114).

Although these protease inhibitors have excellent properties there is a constant high medical need for novel protease inhibitors that are able to combat a broad spectrum of mutants of HIV with little variance in fold resistance, have a good bioavailability and experience little or no effect on their potency due to plasma protein binding.

It has surprisingly been found that a compound of formula (I) showed an enhanced anti-viral activity compared to e.g. amprenavir, lopinavir, nelfinavir or ritonavir when tested on a HIV mutant strain.

The present invention concerns a compound of formula (I)

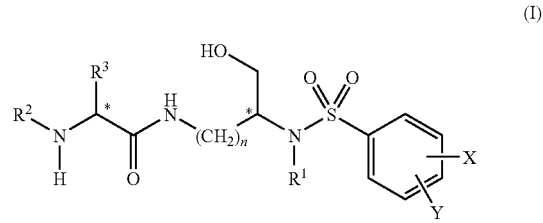

(I)

and when the compound of formula I comprises an amino group, pharmaceutically acceptable ammonium salts thereof, wherein n is 3 or 4, wherein X is H and Y is a straight or branched alkyl group of 1 to 6 carbon atoms substituted with a nitrogen or wherein X and Y are the same and are each a straight or branched alkyl group of 1 to 6 carbon atoms substituted with a nitrogen, wherein $R^1$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the allyl part thereof, wherein $R^2$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{2A}$—CO—, $R_{2A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

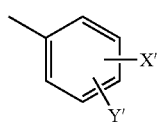

a picolyl group selected from the group consisting of

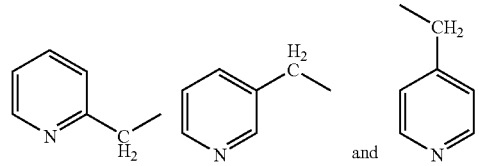

a picolyloxy group selected from the group consisting of

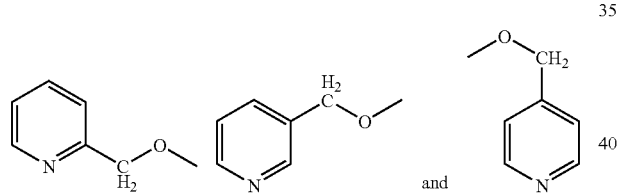

a substituted pyridyl group selected from the group consisting of

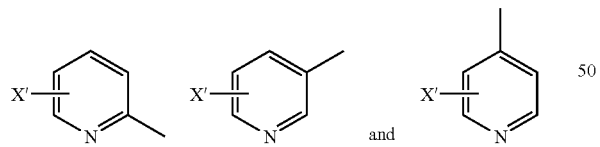

a group selected from the group consisting of

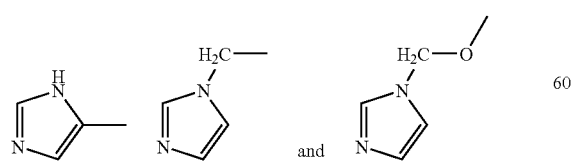

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, wherein $R^4$ and $R^5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein $R^3$ is selected from the group consisting of a diphenylmethyl group of formula IV

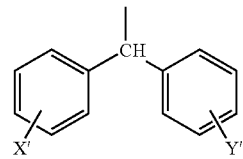

a naphthyl-1-$CH_2$— group of formula V

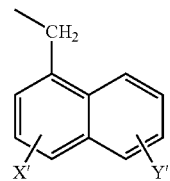

a naphthyl-2-$CH_2$— group of formula VI

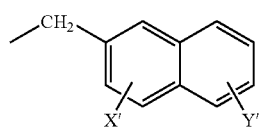

a biphenylmethyl group of formula VII

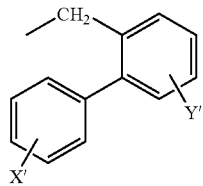

and an (anthracen-9-yl)-methyl group of formula VIII

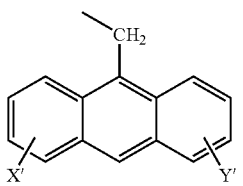

Preferably the compounds according to the invention have the following stereo isomeric form as depicted in formula (II)

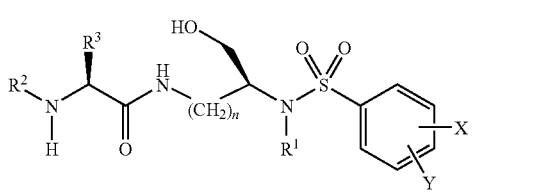

Preferred are the compounds wherein $R^1$ is iso-butyl and n=4; more preferred are those compounds wherein $R^2$ is $CH_3O_2C—$ and even more preferred are those compounds wherein $R^3$ is

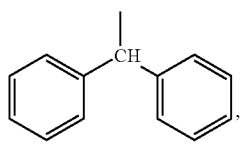

while the most preferred compounds are those wherein X is H and Y is $—CH_2NH_2$.

The most preferred compound is represented by formula (III)

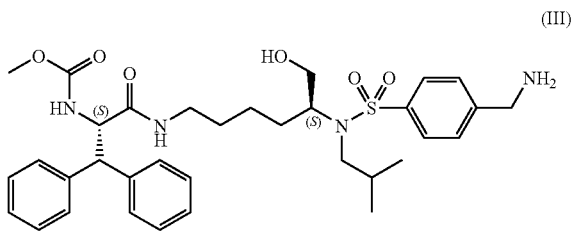

Furthermore, the present invention relates to pharmaceutical preparations, which as active constituents contain an effective dose of at least one of the compounds of formula (I, II or III) in addition to customary pharmaceutically innocuous excipients and auxiliaries. The pharmaceutical preparations normally contain 0.1 to 90% by weight of a compound of formula (I, II or III). The pharmaceutical preparations can be prepared in a manner known per se to one of skill in the art. For this purpose, at least one of a compound of formula (I, II or III), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals, which contain a compound according to the invention, can be administered orally using e.g. including suspensions, capsules, tablets, sachets, solutions, suspensions, emulsions; parenterally using e.g. subcutaneous, intravenous, intramuscular, intrasternal injection or infusion techniques; rectally using e.g. suppositories; intravaginally; by inhalation, or topically. The preferred administration being dependent on the individual cases e.g., the particular course of the disorder to be treated. Oral administration is preferred.

The person skilled in the art is familiar on the basis of his expert knowledge with the auxiliaries, which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefore such as solubilizers, emulsifiers or further auxiliaries, are brought into solution, suspension, or emulsion. The compounds of formula (I), (II) or (III) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I, II or III) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

Due to their favorable pharmacological properties, particularly their activity against multi-drug resistant HIV protease enzymes, the compounds of the present invention are useful in the treatment of individuals infected by HIV and for the prophylaxis of these individuals.

The prophylaxis treatment can be advantageous in cases where an individual has been subjected to a high risk of exposure to a virus, as can occur when individual has been in contact with an infected individual where there is a high risk of viral transmission. As an example, prophylactic administration of said compounds would be advantageous in a situation where a health care worker has been exposed to blood from an HIV-infected individual, or in other situations where an individual engaged in high-risk activities that potentially expose that individual to HIV.

In general, the compounds of the present invention may be useful in the treatment of warm-blooded animals infected with viruses whose existence is mediated by, or depends upon, the protease enzyme. Conditions which may be prevented or treated with the compounds of the present invention include, but is not limited to, treating a wide range of states of HIV infection: AIDS, ARC (Aids Related Complex), both symptomatic and asymptomatic, and actual or potential exposure to HIV. The compounds of the present are also useful for treating progressive generalized lymphadenophaty, Kaposi's syndrome, thrombocytopenia purpurea, AIDS-related neurological conditions such as AIDS dementia complex, multiple sclerosis, tropical parapesis, and also anti-HIV antibody positive and HIV-positive conditions, including such conditions in asymptomatic patients. For example, the compounds of this invention are useful in treating infection by HIV after suspected past exposure to HIV by e.g., blood transfusion, exchange of body fluids, bites, accidental needle stick, or exposure to patient blood during surgery. The term prevention includes prophylaxis of HIV infection and prophylaxis of the evolution of HIV infection to AIDS.

The compounds of the present invention or any derivative thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

In a preferred embodiment, the invention relates to the use of a compound of formula (I, II or III) or any derivative thereof in the manufacture of a medicament for treating or combating infection or disease associated with multi-drug resistant retrovirus infection in a mammal, in particular HIV-1 infection. Thus, the invention also relates to a method of treating a retroviral infection, or a disease associated with multi-drug resistant retrovirus infection comprising administering to a mammal in need thereof an effective amount of a compound of formula (I, II or III) or a derivative thereof.

In another preferred embodiment, the present invention relates to the use of formula (I, II or III) or any derivative thereof in the manufacture of a medicament for inhibiting a protease of a multi-drug resistant retrovirus in a mammal infected with said retrovirus, in particular HIV-1 retrovirus.

In another preferred embodiment, the present invention relates to the use of formula (I, II or III) or any derivative thereof in the manufacture of a medicament for inhibiting multi-drug resistant retroviral replication, in particular HIV-1 replication. Also, the combination of an antiretroviral compound and a compound of the present invention can be used as a medicine. Thus, the present invention also relates to a product or composition containing (a) a compound of the present invention (according to formula (I, II or III)), and (b) another antiretroviral compound, as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors.

The compounds of the present invention may also be administered in combination with modulators of the metabolization following application of the drug to an individual. These modulators include compounds that interfere with the metabolization at cyto-chromes, such as cytochrome P450. Some modulators inhibit cytochrome P450. It is known that several isoenzymes exist of cytochrome P450, one of which is cytochrome P450 3A4. Ritonavir is an example of a modulator of metabolization via cytochrome P450. Interesting compounds having an effect at cytochrome P450 include those compounds containing a thiazolyl, imidazolyl or pyridinyl moiety. Such combination therapy in different formulations may be administered simultaneously, separately or sequentially. Alternatively, such combination may be administered as a single formulation, whereby the active ingredients are released from the formulation simultaneously or separately.

Such modulator may be administered at the same or different ratio as the compound of the present invention. Preferably, the weight ratio of such modulator vis-à-vis the compound of the present invention (modulator: compound of the present invention) is 1:1 or lower, more preferable the ratio is 1:3 or lower, suitably the ratio is 1:10 or lower, more suitably the ratio is 1:30 or lower.

The combination may provide a synergistic effect, whereby viral infectivity and its associated symptoms may be prevented, substantially reduced, or eliminated completely. Combinations of the compounds of formula (I, II or III) with another HIV protease inhibitor as cytochrome $P_{450}$ inhibitor can act synergistically, in an additive way or antagonistically. This can be assessed in an experimental setting where the potency of different ratios of the two HIV-protease inhibitors is measured. Results can be plotted in an isobologram graph according to the method described by Chou and Talalay (Adv. Enzyme Regul. 22: 27-55, 1984) Synergism between two inhibitors would mean a more potent combination therapy, but with no increase in undesired side effects.

Another aspect of the present invention concerns a kit or container comprising a compound of formula (I, II or III) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et at. *Antimicrob Agents Chemother,* 1998; 42(2):269-276).

It is to be understood that the terms "HIV protease" and "HIV aspartyl protease" are used interchangeably and include the aspartyl protease encoded by HIV type 1 or 2.

"Straight alkyl group of 1 to 6 carbon atoms" includes for example, methyl, ethyl, propyl, butyl, pentyl, hexyl.

"Branched alkyl group of 3 to 6 carbon atoms" includes for example, iso-butyl, tert-butyl, 2-pentyl, 3-pentyl, etc.

It is to be understood that a "cycloalkyl group having 3 to 6 carbon atoms" includes for example, cyclopropyl, cyclobutyl, cyclopentyl, cyclocyclohexyl (i.e., $C_6H_{11}$).

Whenever the term "substituted" is used in defining the compounds of formula (I, II or III), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

The salts of compounds of formula (I), (II) or (III) are those wherein the counter ion is pharmaceutically or physiologically acceptable. However, salts having a pharmaceutically unacceptable counter ion may also find use, for example, in the preparation or purification of a pharmaceutically acceptable compound of formula (I), (II) or (III). All salts, whether pharmaceutically acceptable or not are included within the ambit of the present invention.

The pharmaceutically acceptable or physiologically tolerable addition salt forms, which the compounds used in the present invention are able to form, can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I), (II) or (III) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms, which the compounds of the present invention are able to form. Examples of such forms are e.g. hydrates, alcoholates and the like.

The present compound used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound would be synthesized by stereospecific methods of preparation. These methods will advantageously employ enantiomerically pure starting materials.

The diastereomeric racemates of formula (I, II or III) can be obtained separately by conventional methods. Appropriate physical separation methods, which may advantageously be employed, are for example selective crystallization and chromatography, e.g. column chromatography.

The absolute configuration of each asymmetric center that may be present in the compounds of formula (I) may be indicated by the stereochemical descriptors R and S, this R and S notation corresponding to the rules described in Pure Appl. Chem. 1976, 45, 11-30.

EXAMPLES

1. Process for the preparation of (S)—(S)-(1-{5-[(4-Aminomethyl-benzenesulfonyl)-isobutyl-amino]-6-hydroxy-hexylcarbamoyl}-2,2-diphenyl-ethyl)-carbamic acid methyl ester (8)

Synthesis of (S)-(5-Benzyloxycarbonylamino-6-hydroxy-hexyl)-carbamic acid tert-butyl ester (2)

Commercially available (S)-2-benzyloxycarbonylamino-6-tert-butoxycarbonylamino-hexanoic acid (1) (14.89 g) was dissolved in 120 mL dry THF. This solution was cooled to −10° C. $BH_3$ (80 mL, 1M in THF) was slowly added and the resulting solution was stirred for 1 hour below −5° C. and was allowed to warm to room temperature overnight. The reaction was quenched with MeOH, evaporated to dryness and use as such in the next reaction.

Synthesis of (S)-(5-Amino-6-hydroxy-hexyl)-carbamic acid tert-butyl ester (3)

The residue from the first reaction was dissolved in MeOH (150 mL) Pd/C (3 g) was added. The mixture was placed under an H2 atmosphere and hydrogenated overnight at RT. Mixture was filtrated over a pad of dicalite, evaporated to dryness. The crude compound was purified by column chromatography using EtOAc-MeOH(NH3) 97-3 as the eluent. After evaporation an overall yield (over 2 steps) of 75% was obtained.

Synthesis of (S)-(6-Hydroxy-5-isobutylamino-hexyl)-carbamic acid tert-butyl ester (4)

(S)-(5-Amino-6-hydroxy-hexyl)-carbamic acid tert-butyl ester (3) (6.85 g) was dissolved in 200 mL CH2Cl2. Isobutyraldehyde (2.67 mL) was added and this solution was stirred for 2 hours. Sodium triacetoxyborohydride (1.1 eq) was added and the solution was stirred for 2 hours at RT. The solution was washed with sat. NaHCO3. The milky organic phase was separated and evaporated to dryness. The residue was purified by column chromatography using 99:1 EtOAc (100%) to EtOAc-MeOH(NH3) 99-1. as the eluent. Fractions containing the product were evaporated yielding 2.60 g (31%) of the title compound.

Synthesis of (S)-{5-[(4-cyano-benzenesulfonyl)-isobutyl-amino]-6-hydroxy-hexyl}-carbamic acid tert-butyl ester (5)

(S)-(6-Hydroxy-5-isobutylamino-hexyl)-carbamic acid tert-butyl ester (4) (1.85 g) was dissolved in 50 mL $CH_2Cl_2$. Triethylamine (1.05 eq) and 4-cyano benzene sulfonylchloride (1 eq) were added and the mixture was stirred overnight. Saturated NaHCO3 (50 mL) was added, the mixture was well shaken. Organic layer was separated, dried on MgSO4, filtrated and evaporated. The crude compound was purified by column chromatography using EtOAc-heptane (1-3) as the eluent. Fractions containing the product were evaporated yielding (1.06 g, 36%) of a solid.

Synthesis of (S)—N-(5-Amino-1-hydroxymethyl-pentyl)-4-cyano-N-isobutyl-benzenesulfonamide (6)

(S)-{5-[(4-cyano-benzenesulfonyl)-isobutyl-amino]-6-hydroxy-hexyl}-carbamic acid tert-butyl ester (5) (1.06 g) was dissolved in 50 mL MeOH. HCl (5-6 N in i-prOH, 30 mL) was added and the mixture was stirred overnight at RT. The mixture was evaporated to dryness and used as such in the next reaction.

Synthesis of (S)—(S)-(1-{5-[(4-Cyano-benzene-sulfonyl)-isobutyl-amino]-6-hydroxy-hexylcarbamoyl}-2,2-diphenyl-ethyl)-carbamic acid methyl ester (7)

(S)—N-(5-Amino-1-hydroxymethyl-pentyl)-4-cyano-N-isobutyl-benzenesulfonamide (6) obtained in the previous reaction was dissolved in 50 mL CH2Cl2. BOP (1.2 eq), and triethylamine (5 eq) were added. After 10 minutes, (S)-2-methoxycarbonylamino-3,3-diphenyl-propionic acid (1 eq) was added and the mixture was stirred at RT for 3 hours. LCMS indicated a complete reaction. The reaction mixture was washed with sat. NaHCO3. The aqueous phase was washed again with 100 mL CH2Cl2. The combined organic layers where dried with MgSO4, filtered over dicalite and evaporated to dryness. The residue was purified by column chromatography with CH2Cl2-MeOH(NH3) (97:3). The appropriate fraction was evaporated to dryness. (1.31 g, 84% yield over 2 steps)

Synthesis of (S)—(S)-(1-{5-[(4-Aminomethyl-benzenesulfonyl)-isobutyl-amino]-6-hydroxy-hexylcarbamoyl}-2,2-diphenyl-ethyl)-carbamic acid methyl ester (8)

(S)—(S)-(1-{5-[(4-Cyano-benzenesulfonyl)-isobutyl-amino]-6-hydroxy-hexyl-carbamoyl}-2,2-diphenyl-ethyl)-carbamic acid methyl ester (7) (1.31 g) was suspended in MeOH containing $NH_3$ (7N). An aqueous suspension of Ra/Ni was added. The mixture was placed under an atmosphere of $H_2$ and stirred at RT. When the reaction was complete, the mixture was evaporated to dryness and the residue was purified by preparative HPLC-MS. After evaporation 0.435 g (34%) off a white solid was obtained. LC-MS: m/z=639; $^1$H-NMR (CDCl$_3$): 7.78 ppm (d, J=8.01, 2H); 7.45 ppm (d, J=7.56, 2H); 7.35-7.15 ppm (m, 10H); 6.61 ppm (br s, 1H, NH); 5.58 ppm (d, J=8.65, 1H, NH); 4.86 ppm (dd, J=9.74, J=9.66, 1H); 4.42 ppm (d, J=10.65, 1H); 4.04 ppm (d, J=15.42, 1H); 4.02 ppm (d, J=15.58, 1H); 3.58 ppm (s, 3H); 3.57-3.52 (m, 4H); 3.11-2.8 (m, 3H); 2.45 (m, 1H); 1.89 (sept, J=7.11, 1H); 1.34 ppm (m, 2H); 1.1 (m, 1H); 0.99-0.96 ppm (m, 6H); 0.95-0.75 (m, 2H).

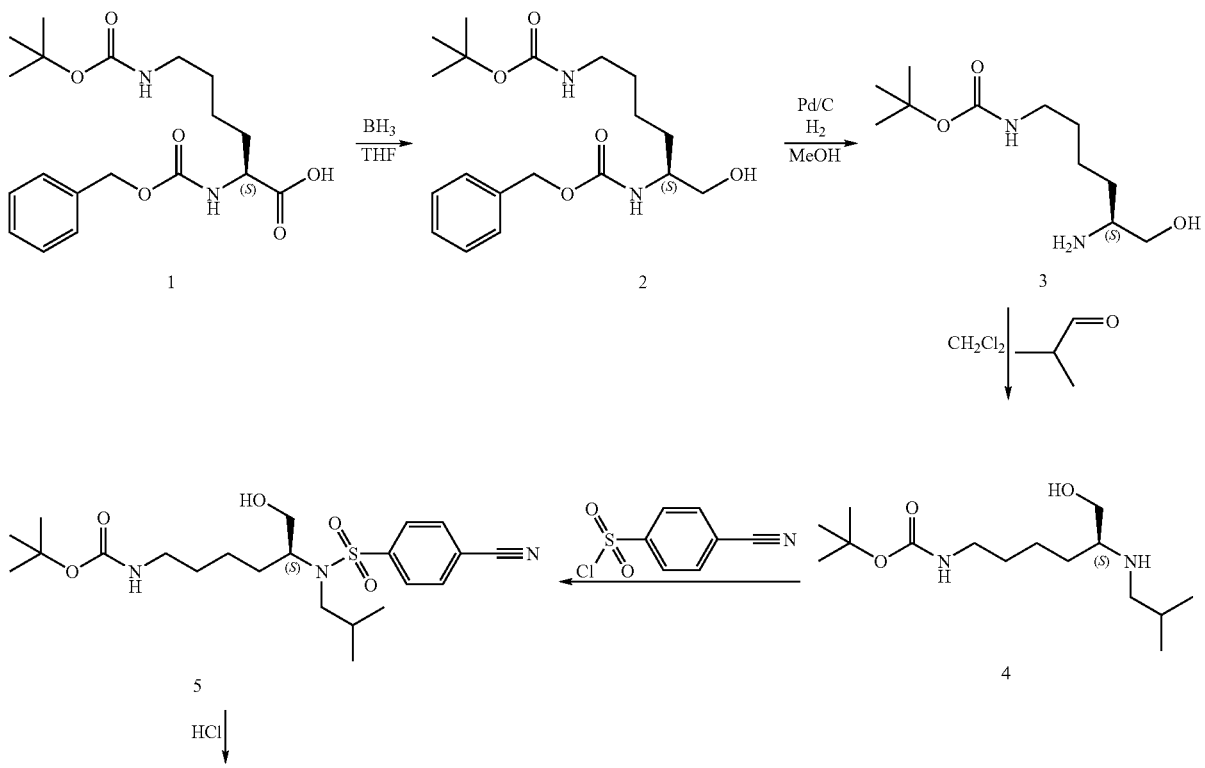

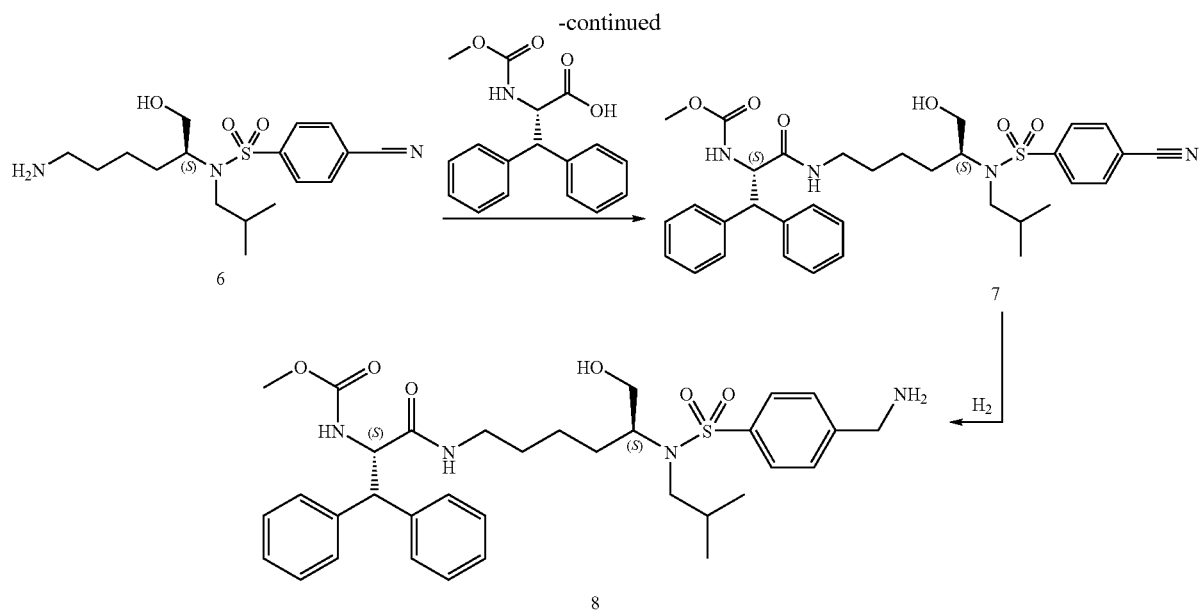

2. Virological Properties of a Compound of the Current Invention

The compound having structural formula (III) was tested in a cellular assay using the MT4-LTR-EGFP cells for anti-viral activity. The assay demonstrated that the compound exhibits potent anti-HIV activity against a wild type laboratory HIV strain (WT IIIB-2-001).

Because of the increasing emergence of drug resistant HIV strains, the present compound was also tested for its potency against a clinically isolated HIV strain harboring several mutations. These mutations are associated with resistance to protease inhibitors and result in viruses that show various degrees of phenotypic cross-resistance to the currently commercially available drugs such as for instance saquinavir, ritonavir, nelfinavir, indinavir and amprenavir. The viral strain tested R13363 contains mutations as indicated below.

| r13363 | V003I, V032I, L035D, M036I, S037N, K043T, M046I, I047V, I050V, K055R, I057K, I062V, L063P, A071L, V082I, I085V, L090M, I093L |
|---|---|

The cellular assay was performed according to the following procedure.

HIV- or mock-infected MT4-LTR-EGFP cells were incubated for three days in the presence of various concentrations of the compound according to the invention. As reference compounds APV, IDV, RTV, NFV, TPV and LPV were used. Upon infection, the viral tat protein activates the GFP reporter. At the end of the incubation period, the GFP signal was measured. In the virus control samples (in the absence of any inhibitor) the maximal fluorescent signal was obtained. The inhibitory activity of the compounds were monitored on the virus-infected cells and were expressed as $EC_{50}$. These values represent the amount of the compound required to protect 50% of the cells from virus infection.

For the compound according to the invention with structural formula (III)

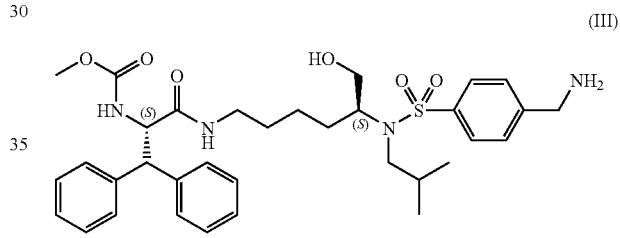

(III)

the following $pEC_{50}$ values were obtained on wild type (IIIB) and clinically isolated HIV strain r13363 harboring several mutations

| $pEC_{50}$_IIIB | $pEC_{50}$-r13363 |
|---|---|
| 7.5 | 7.5 |

For the reference compounds APV, IDV, RTV, NFV, TPV and LPV the following $pEC_{50}$ values were obtained on wild type (IIIB) and clinically isolated HIV strain r13363 harboring several mutations

| | HIV-AVE-MT4LTREGFP-IIIB $pEC_{50}$ | HIV-AVE-MT4LTREGFP-r13363 $pEC_{50}$ |
|---|---|---|
| APV = | 7.3 = | 5.0 |
| IDV = | 7.4 = | 6.4 |
| RTV = | 7.2 = | 5.0 |
| NFV = | 7.2 = | 5.8 |
| TPV = | 6.3 = | 6.3 |
| LPV = | 7.9 = | 6.2 |

The invention claimed is:

1. A compound of formula (I)

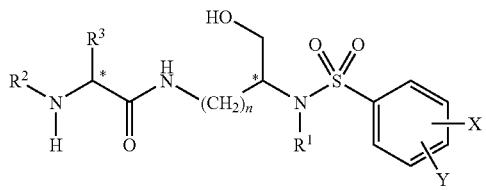

or when the compound of formula I comprises an amino group, a pharmaceutically acceptable ammonium salt thereof, wherein n is 3 or 4, wherein X is H and Y is a straight or branched alkyl group of 1 to 6 carbon atoms substituted with a nitrogen or wherein X and Y are the same and are each a straight or branched alkyl group of 1 to 6 carbon atoms substituted with a nitrogen, wherein $R^1$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein $R^2$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{2A}$—CO—, $R_{2A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

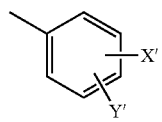

a picolyl group selected from the group consisting of

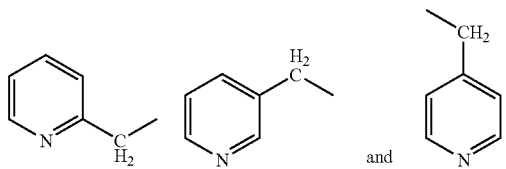

a picolyloxy group selected from the group consisting of

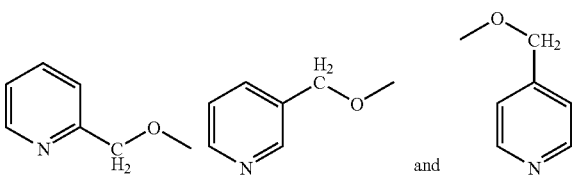

a substituted pyridyl group selected from the group consisting of

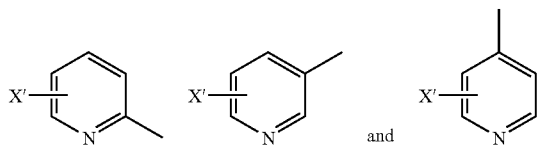

a group selected from the group consisting of

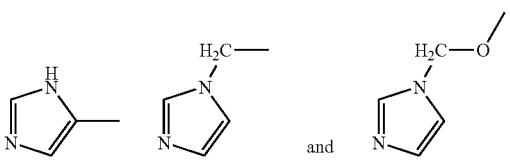

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, wherein $R^4$ and $R^5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein $R^3$ is selected from the group consisting of a diphenylmethyl group of formula IV

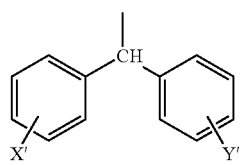

a naphthyl-1-CH$_2$— group of formula V

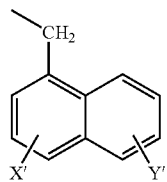

a naphthyl-2-CH$_2$— group of formula VI

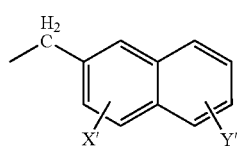

a biphenylmethyl group of formula VII

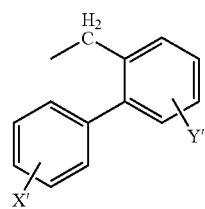

and an (anthracen-9-yl)-methyl group of formula VIII

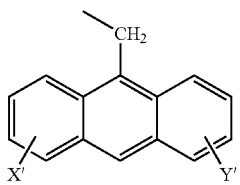

2. A compound of formula (II)

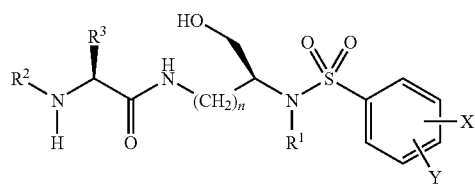

and when the compound of formula II comprises an amino group, pharmaceutically acceptable ammonium salts thereof, wherein n is 3 or 4, wherein X is H and Y is a straight or branched alkyl group of 1 to 6 carbon atoms substituted with a nitrogen or wherein X and Y are the same and are each a straight or branched alkyl group of 1 to 6 carbon atoms substituted with a nitrogen, wherein R$^1$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein R$^2$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula R$_{2A}$—CO—, R$_{2A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —CH$_2$OH, —CF$_3$, —CH$_2$CF$_3$, —CH$_2$CH$_2$CF$_3$, pyrrolidinyl, piperidinyl, 4-morpholinyl, CH$_3$O$_2$C—, CH$_3$O$_2$CCH$_2$—, Acetyl-OCH$_2$CH$_2$—, HO$_2$CCH$_2$—, 3-hydroxyphenyl, 4-hydroxyphenyl, 4-CH$_3$OC$_6$H$_4$—CH$_2$—, CH$_3$NH—, (CH$_3$)$_2$N—, (CH$_3$CH$_2$)$_2$N—, (CH$_3$CH$_2$CH$_2$)$_2$N—, HOCH$_2$CH$_2$NH—, CH$_3$OCH$_2$O—, CH$_3$OCH$_2$CH$_2$O—, C$_6$H$_5$CH$_2$O—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

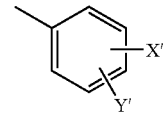

a picolyl group selected from the group consisting of

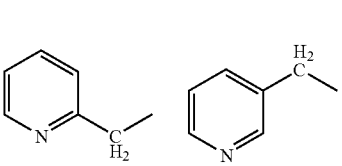

a picolyloxy group selected from the group consisting of

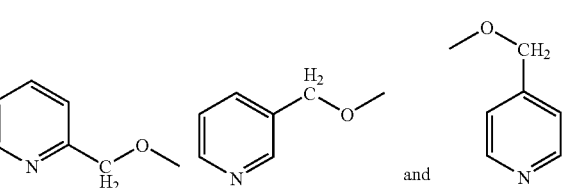

a substituted pyridyl group selected from the group consisting of

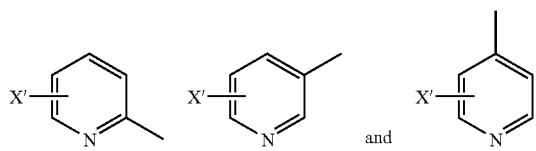 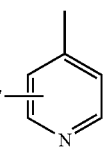

a group selected from the group consisting of

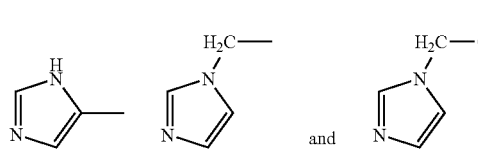

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, wherein $R^4$ and $R^5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein $R^3$ is selected from the group consisting of a diphenylmethyl group of formula IV

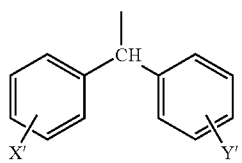

a naphthyl-1-$CH_2$— group of formula V

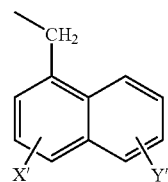

a naphthyl-2-$CH_2$— group of formula VI

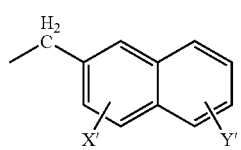

a biphenylmethyl group of formula VII

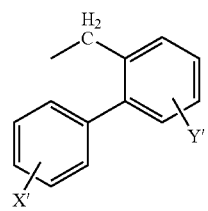

and an (anthracen-9-yl)-methyl group of formula VIII

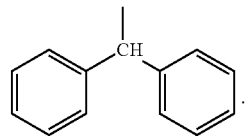

3. A compound according to claim 2 wherein $R^1$ is isobutyl and n is 4.

4. A compound according to claim 3 wherein $R^2$ is $CH_3O_2C$—.

5. A compound according to claim 4 wherein $R^3$ is

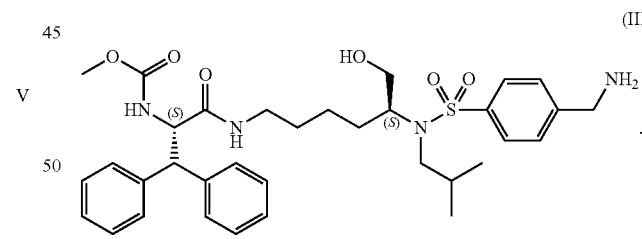

6. A compound according to claim 5 wherein X is H and Y is —$CH_2NH_2$.

7. A compound having the formula (III)

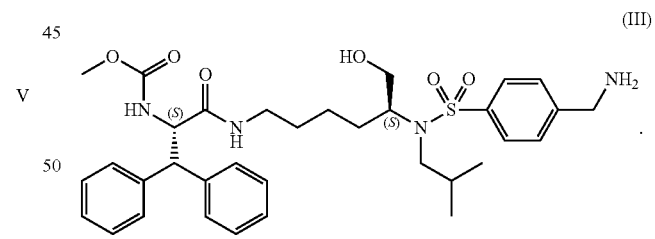

8. A pharmaceutical composition comprising an effective amount of at least one compound as claimed in claim 1 and a pharmaceutically tolerable excipient.

9. A composition comprising at least (a) a compound of formula (I), (II) or (III) as claimed in claim 1 and, (b) a second antiretroviral agent for the simultaneous, separate or sequential use.

10. A pharmaceutical composition comprising an effective amount of at least one compound as claimed in claim 2 and a pharmaceutically tolerable excipient.

11. A pharmaceutical composition comprising an effective amount of at least one compound as claimed in claim 3 and a pharmaceutically tolerable excipient.

12. A pharmaceutical composition comprising an effective amount of at least one compound as claimed in claim 4 and a pharmaceutically tolerable excipient.

13. A pharmaceutical composition comprising an effective amount of at least one compound as claimed in claim 5 and a pharmaceutically tolerable excipient.

14. A pharmaceutical composition comprising an effective amount of at least one compound as claimed in claim 6 and a pharmaceutically tolerable excipient.

15. A pharmaceutical composition comprising an effective amount of at least one compound as claimed in claim 7 and a pharmaceutically tolerable excipient.

16. A composition comprising at least (a) a compound of formula (I), (II) or (III) as claimed in claim 2 and, (b) a second antiretroviral agent for the simultaneous, separate or sequential use.

17. A composition comprising at least (a) a compound of formula (I), (II) or (III) as claimed in claim 3 and, (b) a second antiretroviral agent for the simultaneous, separate or sequential use.

18. A composition comprising at least (a) a compound of formula (I), (II) or (III) as claimed in claim 4 and, (b) a second antiretroviral agent for the simultaneous, separate or sequential use.

19. A composition comprising at least (a) a compound of formula (I), (II) or (III) as claimed in claim 5 and, (b) a second antiretroviral agent for the simultaneous, separate or sequential use.

20. A composition comprising at least (a) a compound of formula (I), (II) or (III) as claimed in claim 6 and, (b) a second antiretroviral agent for the simultaneous, separate or sequential use.

21. A composition comprising at least (a) a compound of formula (I), (II) or (III) as claimed in claim 7 and, (b) a second antiretroviral agent for the simultaneous, separate or sequential use.

* * * * *